United States Patent [19]
Fischer

[11] Patent Number: 5,387,103
[45] Date of Patent: Feb. 7, 1995

[54] SYRINGE APPARATUS FOR DELIVERING TOOTH COMPOSITES AND OTHER SOLID YET PLIABLE MATERIALS

[75] Inventor: Dan E. Fischer, Sandy, Utah

[73] Assignee: Ultradent Products, Inc., South Jordan, Utah

[21] Appl. No.: 19,268

[22] Filed: Feb. 16, 1993

[51] Int. Cl.⁶ .................................................. A61C 5/04
[52] U.S. Cl. ......................................... 433/89; 433/90; 604/59; 604/218; 222/575
[58] Field of Search ....................... 433/89, 90; 604/59, 604/61, 211, 218, 173, 11, 15, 57, 60, 311, 191; 222/575

[56] References Cited

U.S. PATENT DOCUMENTS

| | | |
|---|---|---|
| D. 277,134 | 1/1985 | Dragan . |
| D. 289,682 | 5/1987 | Dragan . |
| D. 292,825 | 11/1987 | Dragan . |
| D. 315,956 | 4/1991 | Dragan . |
| 2,515,956 | 7/1950 | Greenberg . |
| 2,537,550 | 1/1951 | Roos . |
| 3,581,399 | 6/1971 | Dragan . |
| 3,724,076 | 4/1973 | Schmitz . |
| 3,884,231 | 5/1975 | Peters . |
| 3,900,954 | 8/1975 | Dragan . |
| 4,198,756 | 4/1980 | Dragan . |
| 4,295,828 | 10/1981 | Rudler . |
| 4,391,590 | 7/1983 | Dougherty . |
| 4,457,712 | 7/1984 | Dragan . |
| 4,472,141 | 9/1984 | Dragan . |
| 4,492,576 | 1/1985 | Dragan . |
| 4,540,405 | 9/1985 | Miller et al. . |
| 4,569,662 | 2/1986 | Dragan . |
| 4,619,613 | 10/1986 | Dragan . |
| 4,643,724 | 2/1987 | Jobe . |
| 4,682,950 | 7/1987 | Dragan . |
| 4,708,650 | 11/1987 | Holewinski et al. . |
| 4,767,326 | 8/1988 | Bennet et al. . |
| 4,768,954 | 9/1988 | Dragan . |
| 4,784,607 | 11/1988 | Francois . |
| 4,863,072 | 9/1989 | Perler . |
| 4,872,936 | 10/1989 | Engelbrecht . |
| 4,915,695 | 4/1990 | Koobs ................. 604/191 |
| 4,963,093 | 10/1990 | Dragan . |
| 5,052,927 | 10/1991 | Discko, Jr. . |
| 5,122,057 | 6/1992 | Discko, Jr. . |

*Primary Examiner*—C. Fred Rosenbaum
*Assistant Examiner*—Perry E. Van Over
*Attorney, Agent, or Firm*—Workman Nydegger Seeley

[57] ABSTRACT

A syringe apparatus is disclosed for delivering a light-cured tooth composite material of a type that is essentially solid, yet pliable. The syringe apparatus comprises a barrel and a plunger which is used to push the composite material through the barrel. The barrel has an outlet end with a divider formed as an integral part thereof. The divider cuts, sectionalizes, and individually compartmentalizes the material as it is pushed to the outlet of the barrel. Thus, the material is extruded into a plurality of individualized sections. Each individualized section of material is contained in a separate compartment having a support surface that optionally extends beyond the outlet end of the barrel. The support surface serves as a cutting plate against which a dental tool can pinch off a discreet portion of the material.

44 Claims, 9 Drawing Sheets

SYRINGE APPARATUS FOR DELIVERING TOOTH COMPOSITES AND OTHER SOLID YET PLIABLE MATERIALS

BACKGROUND

1. Field of the Invention

This invention relates to syringe systems that are used for extruding materials therefrom, and more particularly to a dental syringe system which more easily provides the potential for separated, more controllable doses of a solid but pliable extrudent as the material is extruded from the syringe system, the material being a light activating composite which cures with exposure to an activating light.

2. Prior State of the Art

The prior art addresses syringes which are constructed to progressively extrude solid, yet pliable materials such as composite materials that are used in clinical dental procedures. The extrudent in dental procedures may be a light-cured composite material. Once the material is extruded from the syringe, it must be moved to the site where the material is to be applied. The material may be extruded directly onto an application site by contacting the site directly with the tip of the syringe. However, such direct placement may cause contamination of a large portion of the material when the application site is unsterile. Thus, direct application is not the best means of application of the extruded material where concern for cross contamination exists and adequate safeguards aren't present.

For the purposes of illustrating the technology of tooth restoration, FIGS. 8 and 9 are featured to show respectively a top tooth and a bottom tooth, 80 and 90, with respective teeth restoration areas 82, and 92, which are to be treated or filled with composite materials.

Typical of dental tooth filling composite materials is their common propensity to shrink while curing or hardening after application to a tooth restoration site, 82, 92. Due to the predictable degree of shrinkage, the dentist must build up the tooth restoration areas, 82, 92, in incremental steps or layers. As shown in FIGS. 8 and 9, the areas to be treated or filled are individual tooth surfaces, such as surfaces 84 and 86 at tooth restoration site 82 on an upper jaw tooth 80, and such as surfaces 94 through 98 at tooth restoration site 92 on a lower jaw tooth 90.

Filling a tooth restoration site, 82, 92, often involves small amounts of composite material. Even when a restoration site is relatively large, small, controllable amounts of the material are preferably used for the application of a layer of light-cured composite material, B, that has been extruded from a syringe, C, (See FIGS. 1A and 1B) and then carefully shaping the layer on and around a prepared tooth surface. The shaped composite material is then exposed to an activating light, D, to instigate the curing and shrinking process of the shaped layer of composite material.

The process of shrinking must be allowed to proceed before applying yet another layer of extruded composite material to the same tooth. The need for sequential layering is understood by those of skill in the art in that with certain preferred bonding agents there is enough adhesion of the dental composite material to the walls of the preparation area, (82, 92) that if the dentist were to apply in a single application the total mass required to fill the preparation area, (82, 92) the material would adhere to both the buccal side and the lingual side of the preparation area, (82, 92) and would then contract the tooth (80, 90) and would tend to pull the cusps of the tooth together causing moderate to extreme post operative discomfort and sensitivity in the tooth (80, 90), as well as other potential side effects therefrom such as premature failure of the restoration. However, by layering the material as shown at layers 86a–86b or 95a–95d in progressive steps and at various angles at which the layers of the extrudent are applied, the drawing or pulling of the cusps together in an uncontrolled shrinkage process will be prevented.

The dentist must properly account for the shrinkage of each layer of the composite material that is applied. Restoration sites, 82, 92, incrementally restored in small layers, will cause the mass of composite material applied thereat to incrementally shrink across the respective smaller layered areas until the dentist has built up the restoration site, 82, 92 to the desired surface morphology of the tooth, 80, 90.

An added benefit of the incremental layering process is the assurance that even the deepest layers of the restoration sites, 82, 92, have an adequate degree of exposure to activating light to cure and shrink properly.

As shown in Prior Art FIGS. 1A and 1B, the dental tool, E, that is used to remove the extrudent, B, from the syringe, C, may be a shaping tool. The shaping and/or placement tool or instrument could be an instrument of any design that is comfortable for the dentist to use. For instance, a spatulating device may be used for applying the material, B, onto a flat surface such as those surfaces shown in FIGS. 8 and 9. The tool could also be a little round section condenser or plugger which is used to place the composite material, by pushing on the end of the tool, into a deeper tooth preparation site such as on a posterior back tooth.

Tools having a cross-sectional area that is cylindrical, such as are used in packing dental composite material into tooth preparation areas, may be clumsy when also used to dig dental composite material out of the end of a syringe. They may also be clumsy for both retaining the material on the operative end of that instrument and then packing it into the bottom of the tooth restoration site. Tools that are not suited for such digging operations, in addition to being somewhat clumsy, tend to be wasteful of the composite material and can incorporate air voids into the material in the process of digging, a detriment which is discussed below.

Using cylindrical, cross-sectional tools to dig out or remove material from a syringe barrel is also undesirable in that many times the pieces of composite material that are thus removed from the syringe are of an irregular shape, such as long, skinny, or strung-out pieces. By the time the resultant irregular shape is approximated over the tooth restoration site and packed in, the material may have incorporated air bubbles or voids, or may inadvertently contact undesired areas such as unprepared tooth surfaces, gum tissue or the like. A further disability is that such irregular pieces of composite material are quite clumsy to precisely place at the tooth restoration site.

As is best seen in Prior Art FIG. 1-A, a spatula, E, is used to remove material from a syringe, C, which the dentist (I) is holding. An assistant or the dentist may also be holding a mouth mirror in one hand. The syringe, C, may require two hands to operate when extruding the composite material, B, because the material, B, is solid enough that many prior art syringes used have a threaded plunger, H, to help extrude the material, B. As the shaping and/or placing tool, E, is manually manipulated to remove the composite material, B, out of the inside of the syringe, C, it is difficult to get predictable quantities of composite material, B, properly situated at the end of instrument, E. In fact, it is not uncommon for masses of the composite material, B, so excavated, to be dropped to the floor of the dental procedure room, and to be thus wasted.

Where the composite material, B, is a light-cured material, the dental assistant, A, will simultaneously try to manually cover the material, B, with the other hand, G, or with a finger or fingers of the same hand, to protect it from activating light, D, radiated from a light source. Such protection is desirable to protect the portions of the material, B, which are not to be removed, from a premature curing process. However, this protective effort by the dental assistant, A, to cover the material, B, is a problem in that the assistant's hand, G, is not free for other and simultaneously required tasks.

In Prior Art FIG. 1A, the dentist, I, digs at the material, B, with a spatula, E, from the inside of the syringe, C, in order to form a mound of the substance material, B, on the end of the instrument, E. A problem with this procedure is that the digging of the material, B, with the instrument, E, tends to interstitially place air bubbles or voids in the material, B. The incorporated air into the composite material, B, will in turn be passed on in the material, B, when it is placed in the preparation site, 82, 92, and could potentially thus degrade the strength or other desired properties of the composite of the restoration.

As shown in Prior Art Figure 1B, the material, B, extends beyond the end of the syringe, C. In such circumstances, the dentists need not dig within the syringe, C, to acquire the necessary mound of the material, B, on the instrument, E. However, such a mound of material, B, may be large, unwieldy, and uncontrollable as the dentist begins to sever the mound with the instrument, E. Even the slightest of misdirection of the instrument, E, may cause the material, B, to become dislodged and fall onto the floor or into the dental patient's bib.

The dentist, I, in order to obtain better control between the instrument, E, and the extrudent mound, B, may use a finger, F, to steady the mound, B, as shown in Prior Art FIG. 1B. Once so held, and in order to obtain a desired and predictable amount of extrudent on the instrument, E, the dentist, I, severs a wedge of the extrudent material, B, with the instrument, E, using a surface of the finger, F, as a cutting surface for the instrument, E, to pinch against.

Using the finger, F, in the procedure potentially provides a ready source of contamination which is in turn carried with the material, B, to the application site, 82, 92. Also, the instrument, E, may have edges which are sharp enough to lacerate or puncture the gloved finger, F, in which case the dental assistant, A, incurs the risk of contagious infection.

BRIEF SUMMARY AND PRINCIPAL OBJECTS OF THE INVENTION

The present invention seeks to resolve the above and other problems which have been experienced in the art. More particularly, the apparatus of this invention constitutes an advancement in syringe art by providing a novel syringe system which achieves each of the objects listed below.

It is an object of the present invention to provide a syringe apparatus which enables a tool to easily pinch off therefrom a wedge of composite material without incorporating in the wedge entrapped air.

It is another important object of the present invention to minimize the loss of composite material which falls off the tool because of difficulty in controlling removal of the material from the syringe apparatus.

It is yet another important object of the invention to provide a syringe apparatus which enables the user to pinch off a wedge of composite material therefrom in discreet and controllable sized wedges having a more predictable and regular shape.

It is an important object of the present invention to provide a syringe apparatus which is fashioned such as to enable pinching off therefrom a composite material wedge so that the wedge can be carefully and predictably placed at the end of the tool when removed.

It is another important object of the present invention to provide a syringe apparatus in which a tool can be used to pinch off a wedge of composite material without having to dig out the wedge from the inside of the syringe apparatus.

It is still a further important object of the present invention to provide a syringe apparatus with an externally disposed support surface against which a tool pinches off a wedge of composite material without having to require another support surface, such as a finger surface.

It is a further important object of the present invention to provide a syringe apparatus which enables a dentist to pinch off a wedge of composite material therefrom while minimizing the risk of laceration or puncture of a person assisting in the process.

It is a further object of the present invention to provide a syringe apparatus which is suited for extrusion of light-activating material by shielding and preventing exposure of significant portions of the extruded material from ambient light and/or from a high intensity lamp used for curing purposes.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention comprises a syringe apparatus of multi-dose capability which enables the removal of material therefrom in a predictable manner and in pieces or wedges of material having a shape that is manageable and controllable upon the end of a shaping and/or placing instrument. The syringe apparatus comprises a barrel and a plunger which is used to push the composite material through the barrel. The barrel has an outlet end with a divider formed as an integral part thereof. The divider cuts, sectionalizes, and individually compartmentalizes the material as it is pushed to the outlet of the barrel. Thus, the material is extruded into a plurality of individualized sections. Each individualized section of material is contained in a separate compartment having a support surface that extends beyond the outlet end of the barrel. The support surface serves as a cutting plate against which a dental instrument can pinch off a discreet portion of the material. Additionally, the syringe apparatus is comprised of materials which block transmissive activating light so as to avoid unwanted exposure of significant portions of the extruded light-activating material.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention and the presently understood best mode for making and using the same will be described with additional specificity and detail through the use of the accompanying drawings in which.

DETAILED DESCRIPTION OF THE PREFERRED EMBODIMENTS

Figure 1:
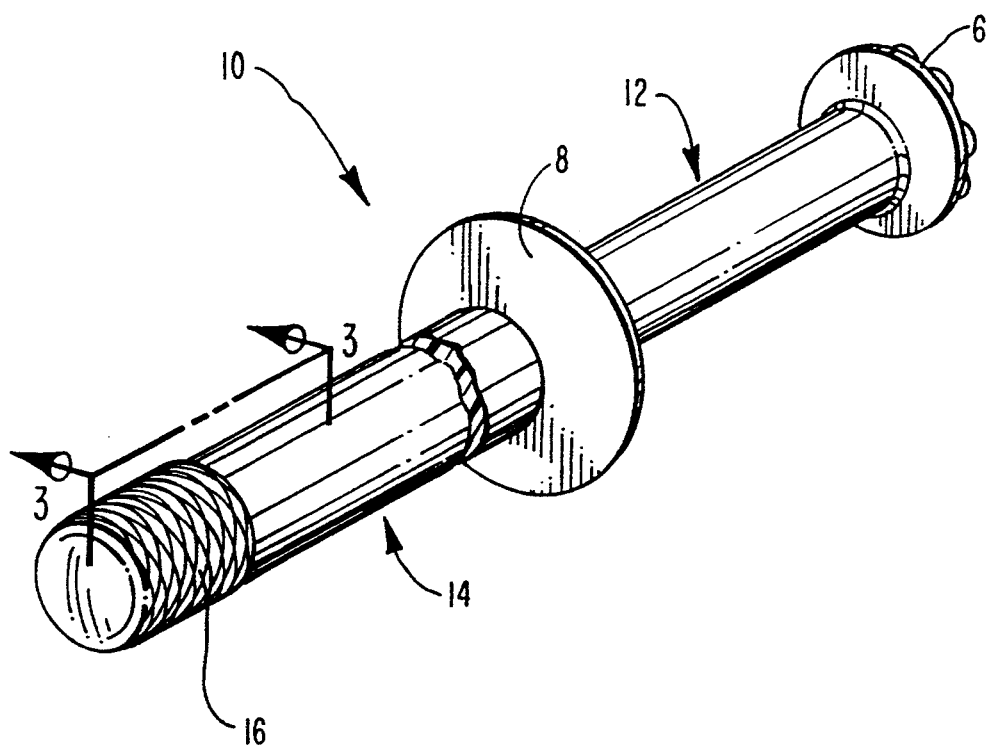
FIG. 1 is a perspective view of one presently preferred embodiment of the syringe apparatus of the present invention.
Figure 2:
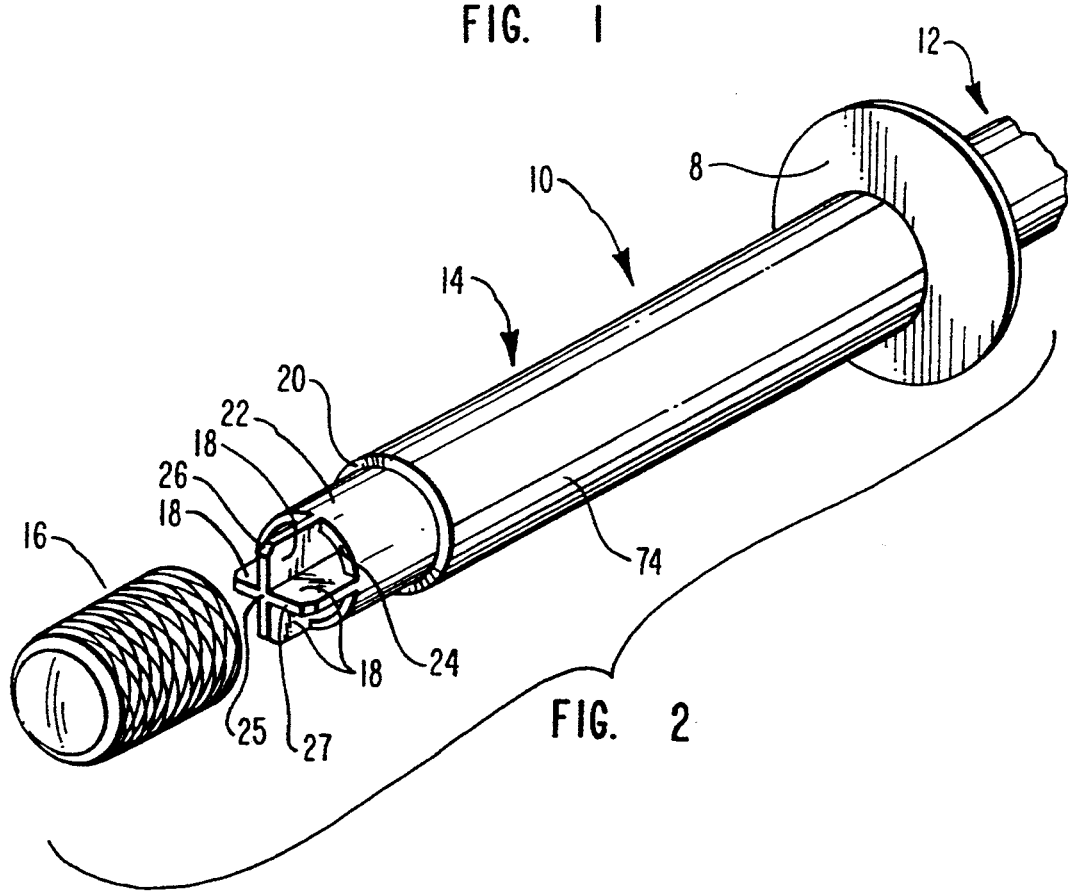
FIG. 2 is a perspective exploded view of the syringe apparatus of FIG. 1 having the cap removed from an end thereof.
Figure 1A:
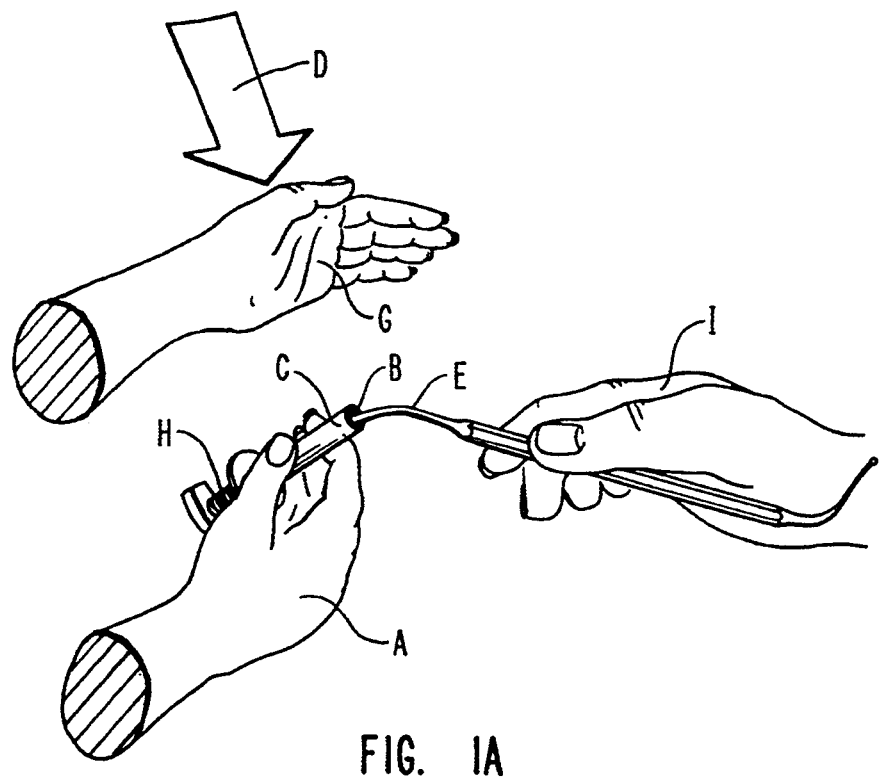
FIG. 1A is a prior art figure showing a perspective view of an instrument being used to dig composite material from within a syringe while the hand of an assistant is used to block activating light from exposing the material within the syringe.
Figure 1B:
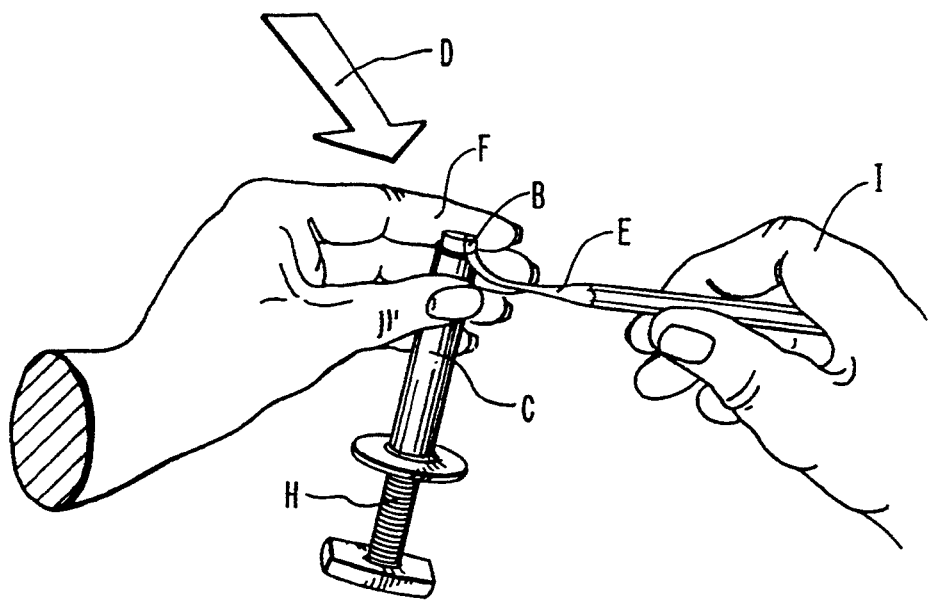
FIG. 1B is a prior art perspective view of an instrument being used to pinch off a wedge of composite material from beyond the end of a syringe, the instrument using a surface of a finger against which to cut off the wedge, while the finger is being simultaneously used to block activating light from exposing the composite material at the end of the syringe.
Figure 5:
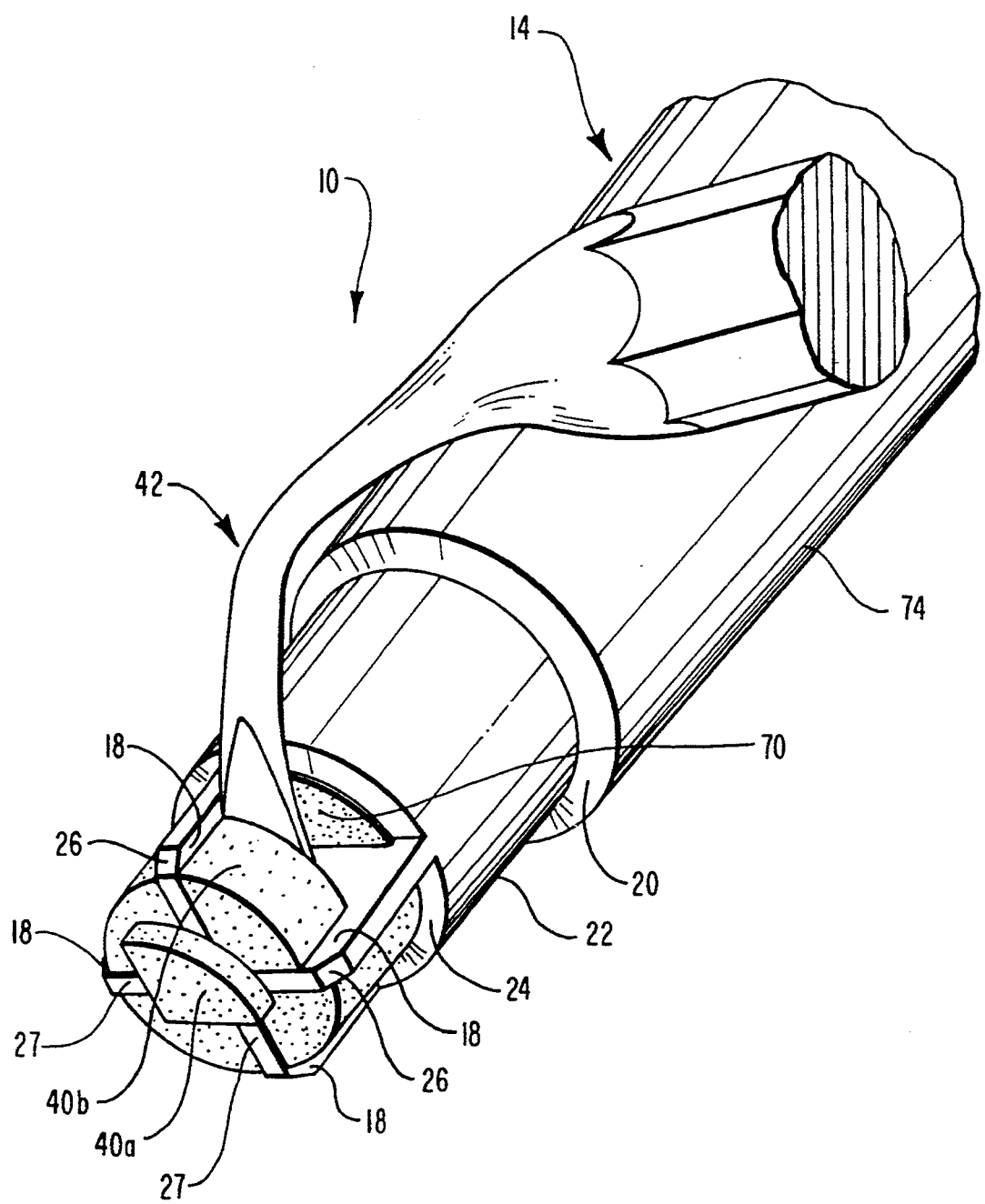
FIG. 5 is a perspective cutaway view of a shaping tool being used to pinch off a wedge of composite material from an end of the syringe apparatus of FIG. 1.

The present invention is broadly described as a syringe apparatus for delivering a material of a type that is essentially solid yet pliable. In one aspect of the invention, the syringe apparatus comprises a barrel means for containing the material, where the barrel means has both an inlet and an outlet end. In a presently preferred embodiment of the invention, as shown in FIGS. 1, 2 and 5, the syringe apparatus is generally indicated at 10, and the syringe barrel is indicated at 14. In a further aspect of the invention, the syringe apparatus comprises a plunger means that is slidably movable through the barrel 14. The presently preferred embodiment illustrates at 12 a suitable plunger.

The barrel 14 has a circular flange 8, intended for the fingers of a user of the syringe apparatus 10. The plunger 12 enters the barrel 14 at the inlet end of the barrel 14 near the circular flange 8, and effects delivery of the material 70 at the outlet end 24 of the barrel 14.

The barrel 14 also has an outer surface 74, which at its distal end 22 has a smaller outer diameter. Barrel 14 also has a shoulder 20 between distal end 22 and surface 74 of barrel 14.

The plunger 12 has a circular disk or head 6 at the proximal end of plunger 12. It is preferable, though not essential, that the plunger 12 and the barrel 14 be small enough that material 70 can be easily extruded by simply pushing plunger 12 through the barrel 14, so as to eliminate the need for a threaded plunger as used in prior art type devices.

Figure 6:
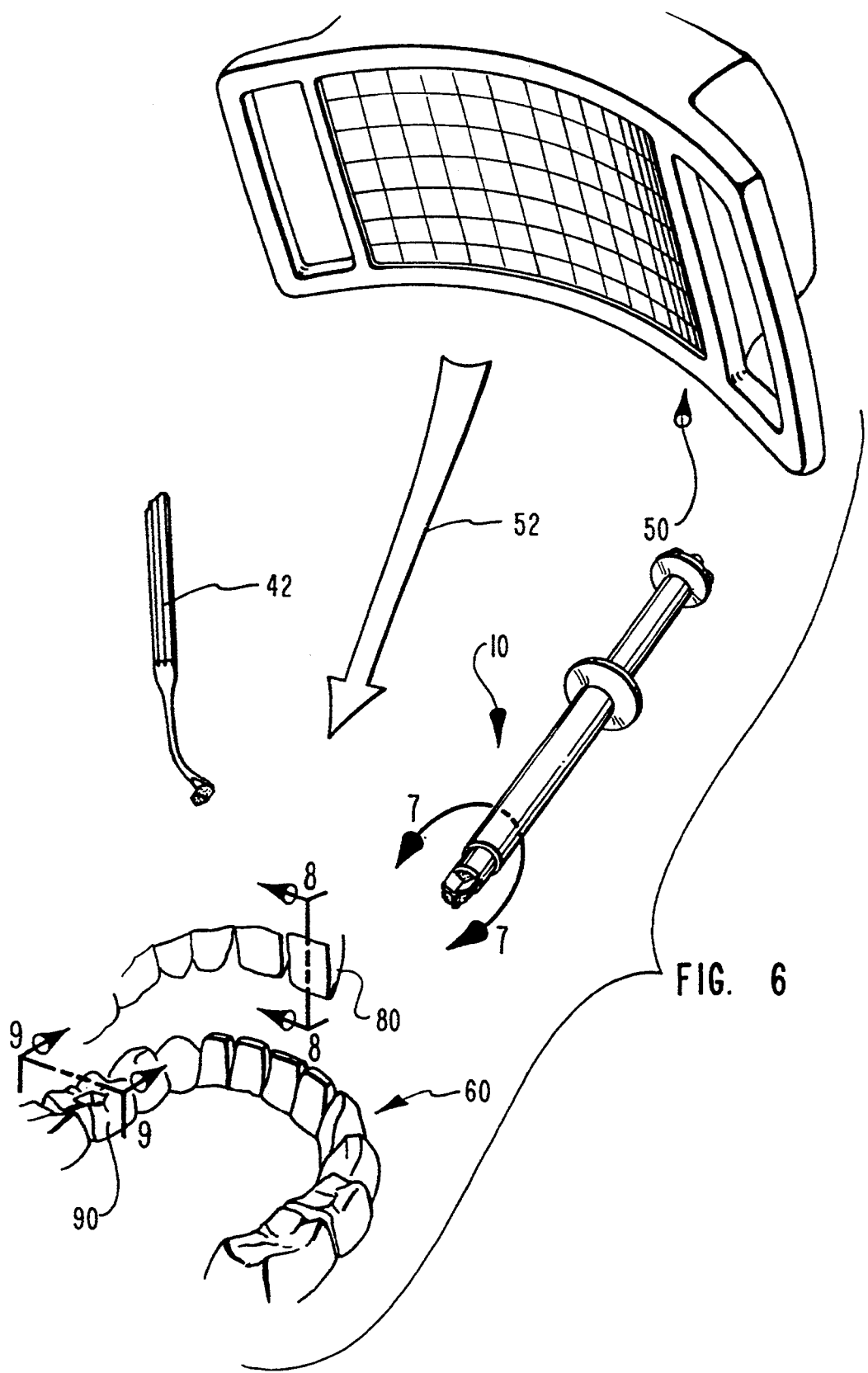
FIG. 6 is a perspective view schematically illustrating a presently preferred embodiment of the present invention being put to use in the context of the dental arts.
Figure 7:
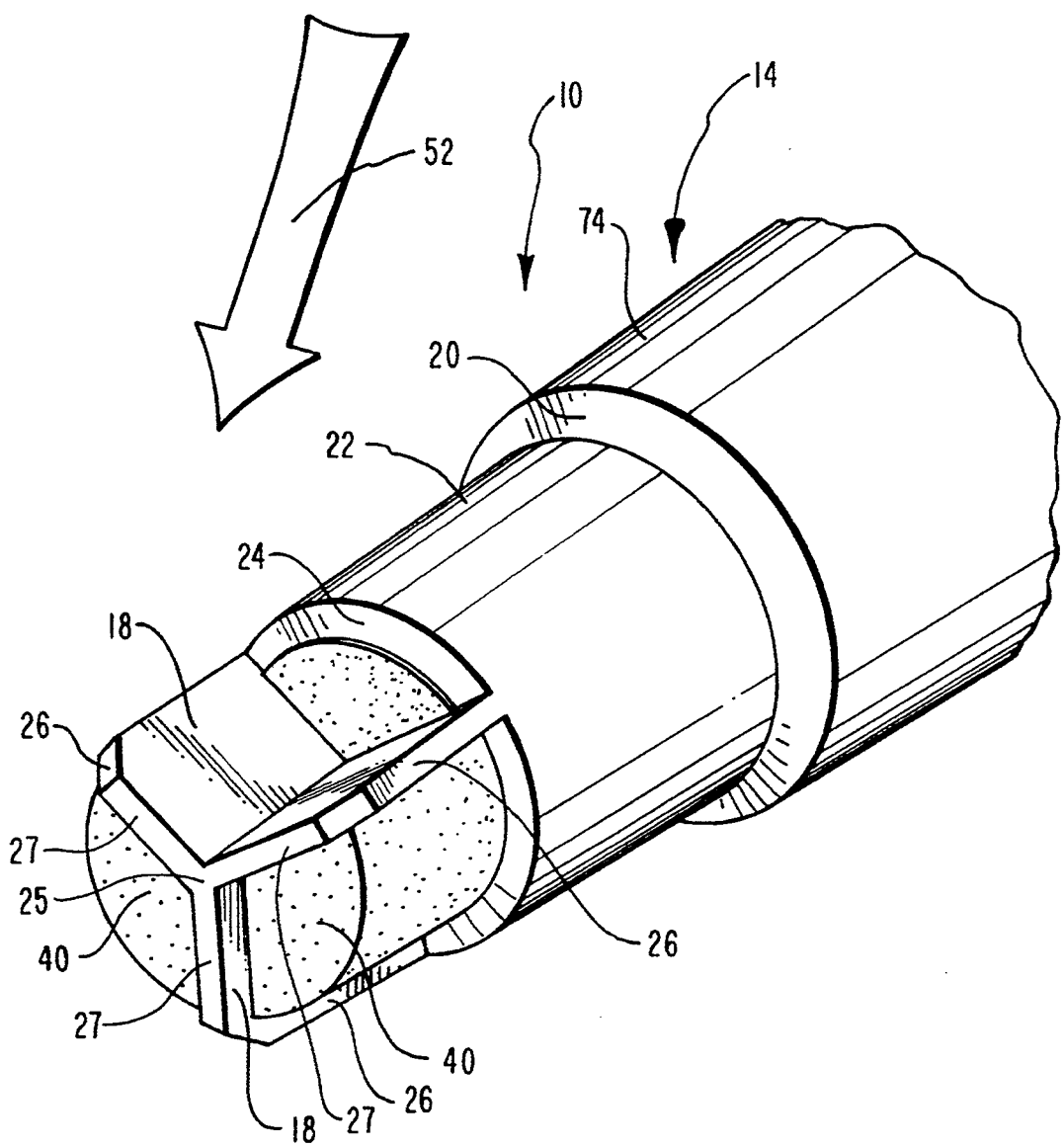
FIG. 7 is an enlarged perspective view of the syringe apparatus according to the present invention which more particularly shows how the divider means can also help shield activating light from affecting uncured portions of extruded material.

As shown in FIGS. 3 through 7, in yet another important aspect of the invention, the barrel 14 further comprises a divider means for sectionalizing and individually compartmentalizing the sectionalized portions 40 of the material 70. As shown best in FIGS. 5 and 7, the material 70 becomes sectionalized and individually compartmentalized as the plunger 12 pushes the material 70 to the outlet end 24 of the barrel 14. In a presently preferred embodiment, the net result of the action between the barrel 14 and its associated divider means with the plunger 12 is that the material 70 will be presented beyond the outlet end 24 of the barrel 14 in a plurality of individualized sections 40. Each of the individualized sections 40 of the material 70 is contained in a separate compartment. Each separate compartment has a support surface 18 which extends beyond the outlet end 24 of the barrel 14. Each section of material 40 lies within a compartment formed by the inside surface 72 of the barrel 14, and at least one support surface 18 of a cutting plate 26. Cutting plates 26 are shown as radially disposed vanes. As shown in FIGS. 5 and 7, each separate compartment accommodates the removal of a selected portion 40 of the sectionalized and compartmentalized part of the material 70.

As illustrated in the presently preferred embodiment, the divider means comprises several cutting plates 26, having on each such cutting plate 26 a support surface 18. Each cutting plate 26 has a leading beveled edge 28 (see FIGS. 3 and 4) which serves to cut the pliable material 70 into individualized sections 40. In a presently preferred embodiment, each of the cutting plates 26 radially extend from a single longitudinal axis 25. The longitudinal axis 25 from which the cutting plates 26 radiate may be centered relative to the center of the barrel 14, or may be offset as shown at 52 in FIGS. 9 and 10 if unequal volumes of sectionalized material are desired, as described further below.

Preferably, the leading beveled edge 28 of each cutting plate 26 lies and is situated within barrel 14. Each cutting plate 26 also includes an opposite trailing edge 27 which extends beyond the outlet end 24 of barrel 14.

As shown in FIG. 5, an instrument 42 is used to sever or pinch off a piece of the sectionalized, compartmentalized pliable material 40. Support surface 18 of cutting plate 26 serves as a cutting surface against which instrument 42 is contacted in order to sever the piece 40 of composite material from the end of the material 70 extending beyond the outlet end 24 of barrel 14. The piece of material may comprise a small portion 40a or a larger portion 40b.

The unextruded portion of the material 70 is shown as being separated from the extruded and pinched off portion 40 from outlet end 24 of barrel 14. The instrument 42 is shown as being a spatula. The spatula easily removes a discreet amount 40a or 40b and regular shape of the pliable material in such a way that the piece of material 40a or 40b is easily manageable and controllable upon the end of instrument 42.

The vanes 26 are shown in FIGS. 2, 4, 5, and 7 as being an integrally molded portion of barrel 14. However, those of skill in the art will note that other ways exist of installing a divider means. It is also noted that the vanes 26 are concentric with the barrel 14. It is intended that radially disposed vanes 26 extend from the longitudinal axis 25 that is shared with the barrel 14 to the inside surface 72 of the barrel 14, such that substantially all of the material 40 that is within barrel 14 will be divided into compartmentalized and sectionalized pieces 40.

Figure 3:
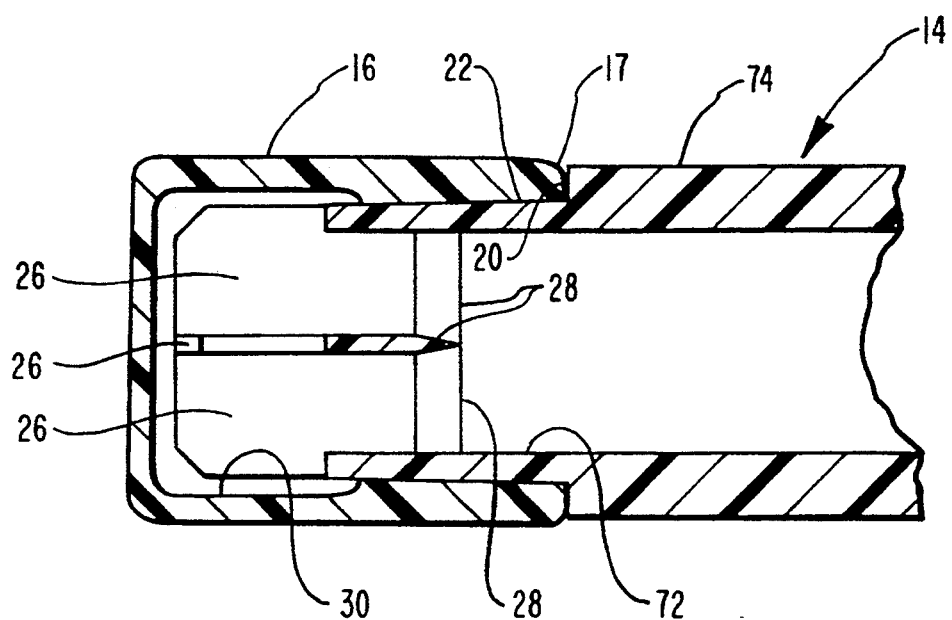
FIG. 3 is a sectional view taken along the 3—3 line of FIG. 1.
Figure 4:
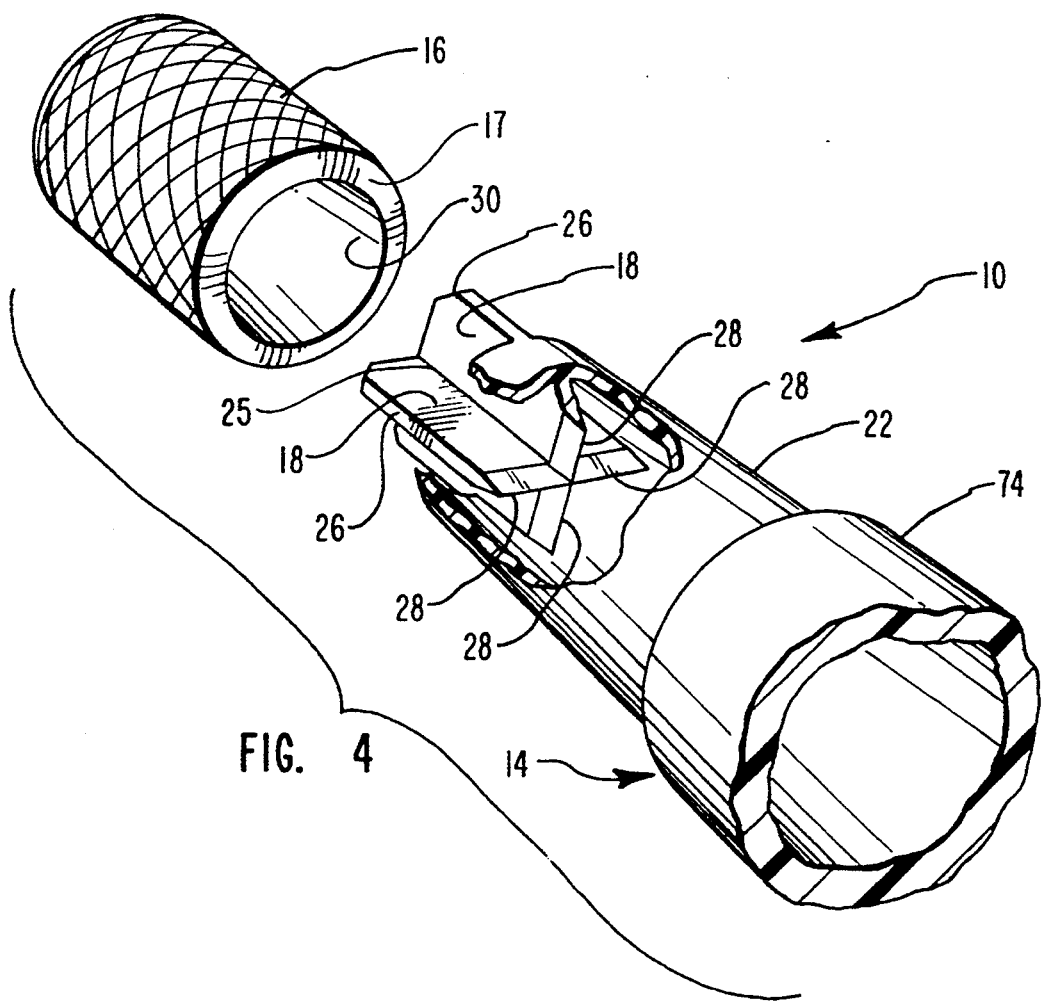
FIG. 4 is a perspective cutaway view of the syringe apparatus of FIG. 1, more particularly illustrating the divider means.

The syringe apparatus 10 further includes a cap means that can be selectively removable from and placed over the individualized sections 40 of the pliable material 70 which have been presented beyond the outlet end 24 of the barrel 14. In a presently preferred embodiment, a cap is seen in FIGS. 1, 2, and 4 at reference numeral 16. FIG. 1 shows the cap 16 installed at the outlet end of the barrel 14. FIG. 2 shows the cap 16 having been removed from the outlet end of the barrel 14. FIG. 3 shows the cap 16 fitting tightly at its proximal end 17 against the shoulder 20 of barrel 14. The tight fit between the proximal end 17 of the cap 16 and the shoulder 20 of barrel 14 is to ensure that the composite material within the barrel 14 is not exposed to ambient conditions. Cap 16 also features a recessed internal surface 30 (see FIG. 3) that overlays and covers all compartmentalized individual sections 40 of the composite material 70 which extend beyond the outlet end 24 of barrel 14.

In the presently preferred embodiment, radially spaced vanes 26 do not contact the internal recessed surface 30 of cap 16 so as to allow ample space for sections 40 when the cap 16 is installed. It is also noted that the cap 16 sealingly fits around external surface 22 of barrel 14 so that the composite material 70 within barrel 14 is sealed off from ambient conditions. In a preferred embodiment of the present invention, the radially spaced vanes 26 do not contact the top inside surface 30 of cap 16, but do contact the inside surface 72 of barrel 14.

A preferable and intended use of a presently preferred embodiment of the present invention is that the syringe apparatus 10 will be used to extrude therefrom a tooth composite material of a type that is essentially solid, yet pliable, and which cures when the material is exposed to an activating light. Other applications and uses of the apparatus are also possible, and are intended as within the scope of the present invention. Preferably, the barrel 14, the radially spaced vanes or cutting plates 26, and support surfaces 18, as well as cap 16 will all be constructed of or coated by a substance having a component that blocks transmission of the activating light which causes the tooth composite material 70 therein to begin curing.

As schematically shown in FIGS. 6 and 7, activating light 52 is being directed from a light source 50 toward syringe apparatus 10. In FIG. 6, instrument 42 is shown as having removed a piece of the composite material from syringe apparatus 10. As seen in FIG. 7, the divider formed by radially spaced plates 26, has support surfaces 18 which will block activating light 52 from exposing the remaining sectionalized portions 40 of the composite material 70 from exposure to light 52. FIG. 1 shows the syringe apparatus 10 essentially sealing the composite material 70 within barrel 14 and cap 16 so that activating light 52 should not expose the material 70 therein when cap 16 and barrel 14 are comprised of a substance which blocks transmission of activating light 52 therethrough.

Figure 8:
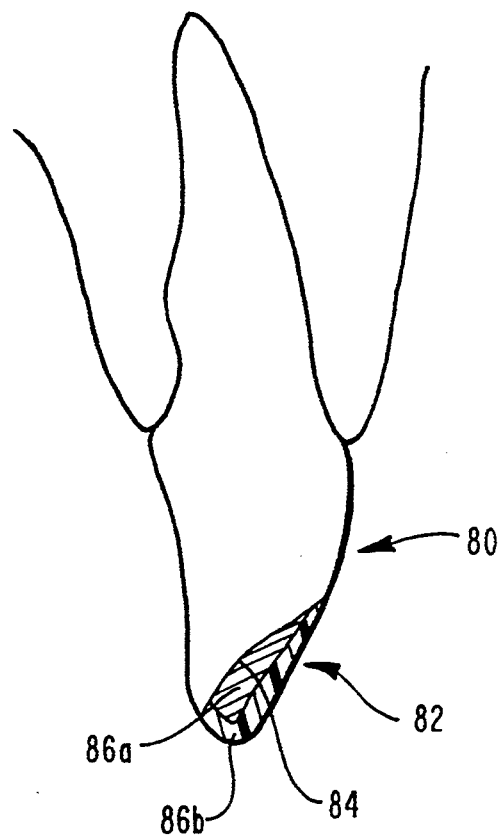
FIG. 8 is a sectional view taken along the 8—8 line of FIG. 6, showing an upper jaw tooth with composite material applied to restore a surface.
Figure 9:
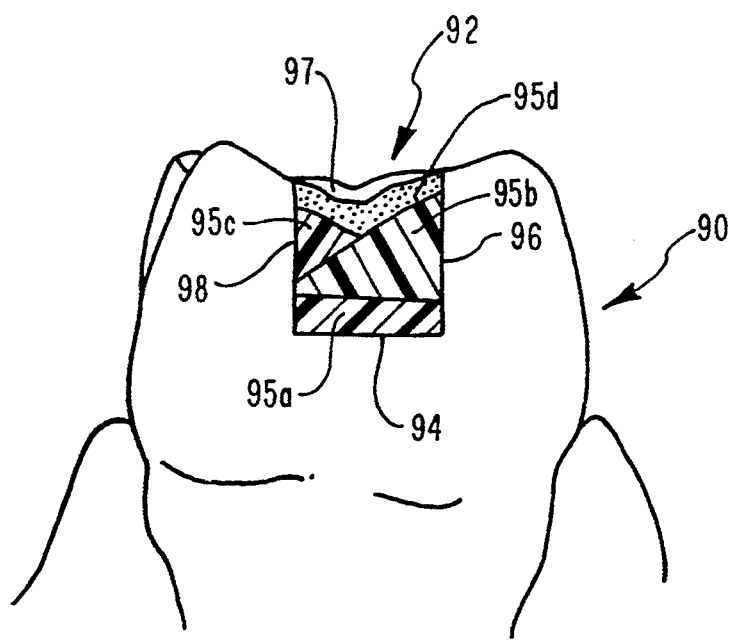
FIG. 9 is a sectional view taken along the 9—9 line of FIG. 6, showing a lower jaw tooth with composite material applied to restore a surface.

As shown in FIG. 6, instrument 42 is a spatula having at its end a removed section 40 of the pliable material 70 that is ready to be applied to tooth 80 or tooth 90, respectively, at tooth restoration sites 82 or 92, at any one of the respective tooth restoration surfaces 84, 86, or 94, 96, 97, 98 (see FIGS. 8 and 9). As previously mentioned, it is desirable that controlled quantities of the removed composite material 70 are applied in layers 86, 95 at various tooth preparation sites 82, 92, to the end that the curing and shrinking process of the composite material 70 will be done in a controlled and precise manner for proper construction of a tooth restoration site.

Figure 10:
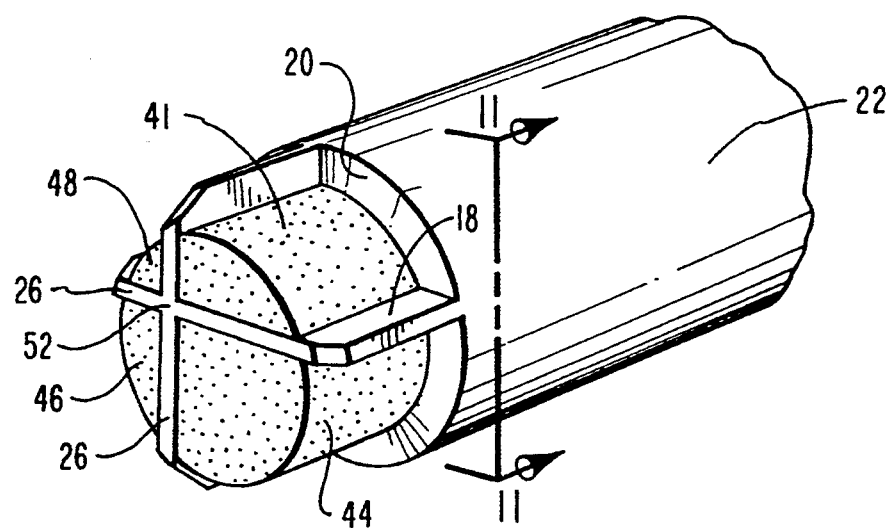
FIG. 10 is a perspective view of another preferred embodiment of the present invention.
Figure 11:
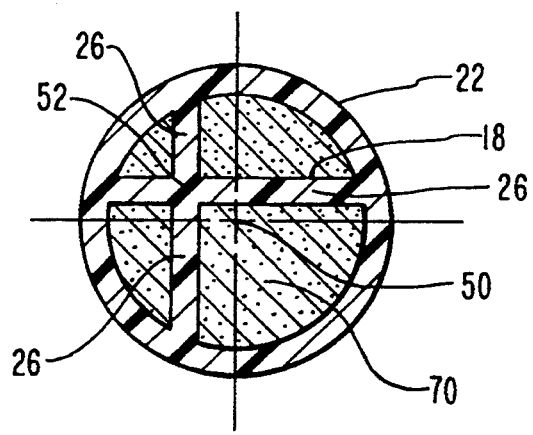
FIG. 11 is a sectional view taken along the 11—11 line of FIG. 10.

Another preferred embodiment of the present invention is shown in FIGS. 10 and 11. The divider means comprises cutting plates 26 which radially extend from a common longitudinal axis 52. The longitudinal axis 52 from which the cutting plates 26 radiate is not the same and is not common with the centrally located longitudinal axis 50 which is the central axis of barrel 14. In this second preferred embodiment, the individualized, compartmentalized portions 41, 44, 46, and 48, are each of different size. It is intended that the instrument 42, as seen in FIG. 6, is used to pinch off, against support surfaces 18, any one of the differently sized portions 41, 44, 46, 48 of the material 70 that is desired.

Figure 12:
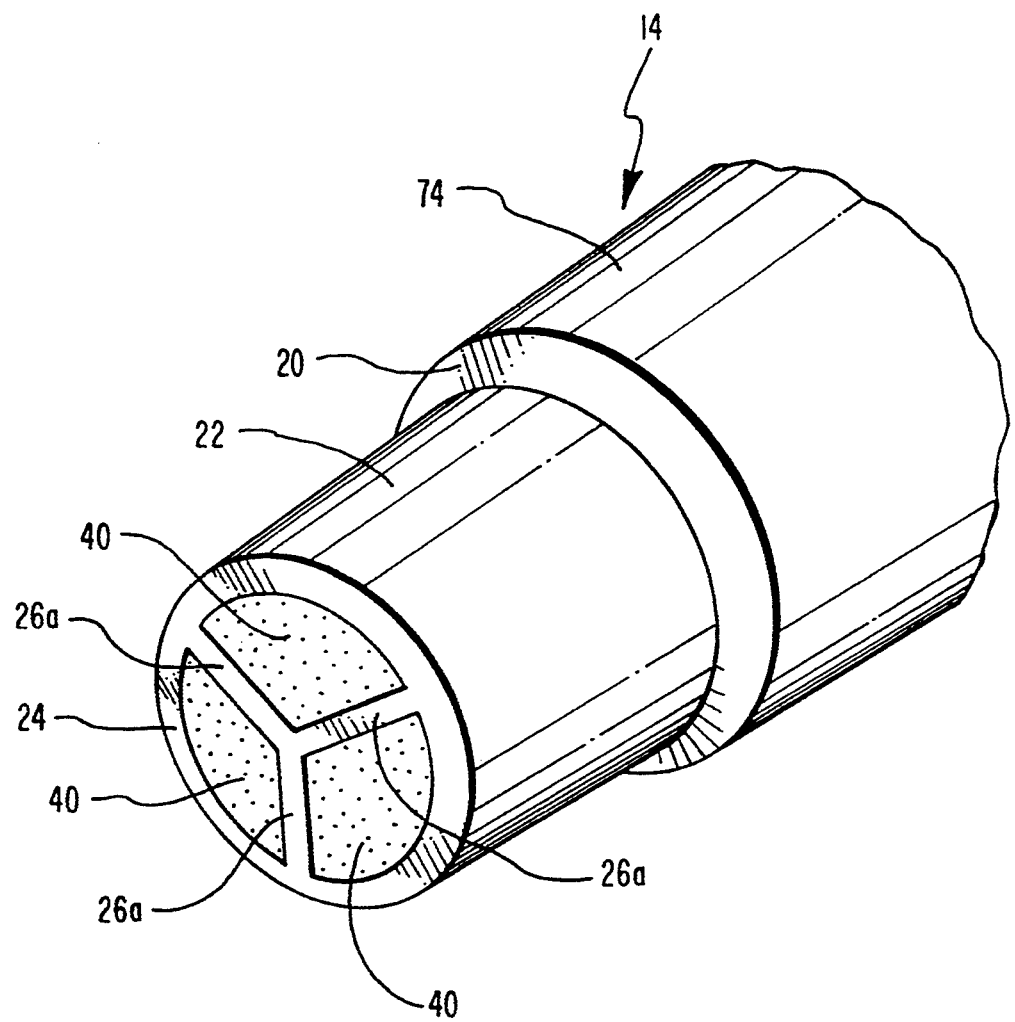
FIG. 12 is a perspective view of another preferred embodiment of the present invention.

FIG. 12 illustrates yet another embodiment of the invention. In FIG. 12, the syringe apparatus is essentially identical to the embodiment as shown and described in FIGS. 1–7, except that in FIG. 12 the vanes 26a terminate at the outlet end 24 of barrel 14. This configuration helps to further protect the extruded sections 40 from activating light.

In summary, the dental syringe system provides discrete and separated doses (or wedges) of a solid but pliable extrudent as the material is extruded from the syringe system. The doses are easily pinched off by a shaping tool against the support surfaces which extend beyond the outlet end of the barrel means. The barrel means, divider means, and cap means block transmissive exposure of the material therein to an activating light so as to prevent premature curing of light activated material therein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A syringe apparatus for delivering a material of a type that is essentially solid, yet pliable, comprising:
    barrel means for containing the material, said barrel means comprising an inlet end and an outlet end;
    plunger means for slidable movement through the barrel means, said plunger means entering the barrel means at said inlet end and effecting delivery of the material at said outlet end as the plunger means is pushed through the barrel means; and
    said barrel means further comprising divider means defining separate compartments for sectionalizing portions of the pliable material as it is pushed through the barrel means, and for individually compartmentalizing the sectionalized portions of the pliable material as it is pushed by said plunger means to the outlet end of said barrel means, such that the pliable material is presented beyond the outlet end of said barrel means in a plurality of individualized sections, each said individualized section being contained in a separate compartment of the divider means, and each said separate compartment having a support surface extending beyond said outlet end of said barrel means to accommodate removal of a selected portion of the sectionalized and compartmentalized part of the material, and wherein said divider means. has a common longitudinal axis with said barrel means, and further comprises at least two planar cutting plates radially extending outward from said common longitudinal axis, each said planar cutting plate having a proximal end and a distal end, the distal end of each said planar cutting plate extending beyond the outlet end of the barrel means and serving as a cutting surface for at least one of said individualized sections.

2. The syringe apparatus as defined in claim 1, wherein said solid, yet pliable material is a light-activated tooth composite material which cures when exposed to an activating light, and wherein both said barrel means and said divider means are comprised of a substance having a component that blocks transmission of said activating light.

3. The syringe apparatus as defined in claim 1, further comprising:
    cap means for both selective removal from and placement over said plurality of individualized sections which are presented beyond the outlet end of said barrel means.

4. The syringe apparatus as defined in claim 2, further comprising:
    cap means, comprised of a substance having a component that blocks transmission of said activating light, for both selective removal from and placement over said plurality of individualized sections which are presented beyond the outlet end of said barrel means.

5. The syringe apparatus as defined in claims 1 or 2, wherein said divider means is formed as an integral part of said outlet end of said barrel means.

6. The syringe apparatus as defined in claim 5, wherein said divider means comprises a plurality of intersecting planar vanes, each said vane having both a beveled leading edge within said barrel means and a trailing edge beyond the outlet end of said barrel means.

7. The syringe apparatus as defined in claim 1 further comprising:
    cap means for both selective removal from and placement over said plurality of individualized sections which are presented beyond the outlet end of said barrel means; and
    wherein said divider means is formed as an integral part of said outlet end of said barrel means.

8. The syringe apparatus as defined in claim 7, wherein said divider means comprises a plurality of intersecting planar vanes, each said vane having both a beveled leading edge within said barrel means and a trailing edge beyond the outlet end of said barrel means.

9. The syringe apparatus as defined in claim 8, wherein said plurality of intersecting planar vanes intersect at a common centrally located longitudinal axis with said barrel means, and wherein each said vane radially extends outward from said common centrally located longitudinal axis.

10. The syringe apparatus as defined in claim 2 further comprising:
    cap means, comprised of a substance having a component that blocks transmission of said activating light, for both selective removal from and placement over said plurality of individualized sections which are presented beyond the outlet end of said barrel means; and
    wherein said divider means is formed as an integral part of said outlet end of said barrel means.

11. The syringe apparatus as defined in claim 10, wherein said divider means comprises a plurality of intersecting planar vanes, each said vane having both a beveled leading edge within said barrel means and a trailing edge beyond the outlet end of said barrel means.

12. The syringe apparatus as defined in claim 1, wherein each said individualized section extends substantially less than the distance between said inlet end of the barrel means and the outlet end of the barrel means.

13. The syringe apparatus as defined in claim 1, wherein said divider means is concentric to and has a noncommon longitudinal axis with said barrel means.

14. The syringe apparatus as defined in claim 13, wherein said divider means further comprises a plurality of intersecting vanes that both intersect at and radially extend outward from said noncommon centrally located longitudinal axis.

15. The syringe apparatus as defined in claim 1, wherein the proximal end of each said planar cutting plate has thereat a beveled cutting edge.

16. The syringe apparatus as defined in claim 1, wherein said barrel means has a cylindrical inside surface extending between the inlet and outlet ends of the barrel means, and wherein each said separate compartment comprises at least a portion of said cylindrical inside surface of said barrel means and at least one of said at least two planar cutting plates.

17. The syringe apparatus as defined in claims 3 or 4, wherein said cap means overlays and essentially seals the outlet end of said barrel means when said cap means is placed over said plurality of individualized sections which are presented beyond the outlet end of said barrel means.

18. The syringe apparatus as defined in claim 17, wherein said barrel means has an external surface and said cap means has an inside surface, said external surface of said barrel means making a sealing contact with the inside surface of said cap means when said cap means is placed over said plurality of individualized sections which are presented beyond the outlet end of said barrel means.

19. The syringe apparatus as defined in claim 18, wherein the inside surface of the cap means defines a space that is large enough so as essentially not to contact said plurality of individualized sections which are presented beyond the outlet end of said barrel means.

20. A syringe apparatus for delivering a light activating tooth composite material of a type that is essentially solid, yet pliable, and which cures when exposed to an activating light, comprising:
barrel means for containing the material, said barrel means comprising an inlet end and an outlet end and being comprised of a substance having a component that blocks transmission of said activating light;
plunger means for slidable movement through the barrel means, said plunger means entering the barrel means at said inlet end and effecting delivery of the material at said outlet end as the plunger means is pushed through the barrel means; and
said barrel means further comprising divider means defining separate compartments for sectionalizing portions of the pliable material as it is pushed through the barrel means, and for individually compartmentalizing the sectionalized portions of the pliable material as it is pushed by said plunger means to the outlet end of said barrel means, such that the pliable material is presented beyond the outlet end of said barrel means in a plurality of individualized sections, each said individualized section being contained in a separate compartment of the divider means, and each said separate compartment having a support surface extending beyond said outlet end of said barrel means to accommodate removal of the selected portion of a sectionalized and compartmentalized part of the material, said divider means being comprised of a substance having a component that blocks transmission of said activating light; and
cap means, comprised of a substance having a component that blocks transmission of said activating light, for selective removal from and placement over said plurality of individualized sections which are presented beyond the outlet end of said barrel means.

21. The syringe apparatus as defined in claim 20, wherein said divider means is formed as an integral part of said outlet end of said barrel means.

22. The syringe apparatus as defined in claim 21, wherein said divider means comprises a plurality of intersecting planar vanes, each said vane having both a beveled leading edge within said barrel means and a trailing edge beyond the outlet end of said barrel means.

23. The syringe apparatus as defined in claim 22, wherein said divider means is formed as an integral part of said outlet end of said barrel means.

24. The syringe apparatus as defined in claim 22, wherein each said individualized section extends substantially less than the distance between said inlet end of the barrel means and the outlet end of the barrel means.

25. The syringe apparatus as defined in claim 20, wherein said divider means is concentric to and has a noncommon longitudinal axis with said barrel means.

26. The syringe apparatus as defined in claim 25, wherein said divider means comprises a plurality of intersecting planar vanes, each said vane having both a beveled leading edge within said barrel means and a trailing edge beyond the outlet end of said barrel means, and wherein said plurality of intersecting vanes both intersect at and radially extending outward from said noncommon centrally located longitudinal axis.

27. The syringe apparatus as defined in claim 20, wherein said divider means is concentric to and has a common centrally located longitudinal axis with said barrel means.

28. The syringe apparatus as defined in claim 27, wherein said divider means further comprises:
at least two planar cutting plates radially extending outward from said common centrally located longitudinal axis, each said planar cutting plate having a proximal end and a distal end, the distal end of each said planar cutting plate extending beyond the outlet end of the barrel means and serving as a cutting surface for at least one of said individualized sections.

29. The syringe apparatus as defined in claim 28, wherein the proximal end of each said planar cutting plate has thereat a beveled cutting edge.

30. The syringe apparatus as defined in claim 28, wherein said barrel means has a cylindrical inside surface extending between the inlet and outlet ends of the barrel means, and wherein each said separate compartment comprises at least a portion of said cylindrical inside surface of said barrel means and at least one of said at least two planar cutting plates.

31. The syringe apparatus as defined in claim 20, wherein said cap means overlays and essentially seals the outlet end of said barrel means when said cap means is placed over said plurality of individualized sections which are presented beyond the outlet end of said barrel means.

32. The syringe apparatus as defined in claim 31, wherein said barrel means has an external surface and said cap means has an inside surface, said external surface of said barrel means making a sealing contact with the inside surface of said cap means when said cap means is placed over said plurality of individualized sections which are presented beyond the outlet end of said barrel means.

33. The syringe apparatus as defined in defined in claim 32, wherein the inside surface of the cap means defines a space that is large enough so as essentially not to contact said plurality of individualized sections which are presented beyond the outlet end of said barrel means.

34. A syringe apparatus for delivering a light activating tooth composite material of a type that is essentially solid, yet pliable, and which cures when exposed to an activating light, comprising:
syringe barrel means for containing the material, said syringe barrel means comprising an inlet end and an outlet end with a cylindrical inside surface of constant inner diameter therebetween, and being comprised of a substance having a component that blocks transmission of said activating light;

plunger means for slidable movement through the syringe barrel means, said plunger means entering the syringe barrel means at said inlet end and effecting delivery of the material at said outlet end as the plunger means is pushed through the syringe barrel means; and said syringe barrel means further comprising divider means defining separate compartments formed as an integral part of said outlet end of said syringe barrel means for sectionalizing portions of the pliable material as it is pushed through the barrel means, and for individually compartmentalizing the sectionalized portions of the pliable material as it is pushed by said plunger means to the outlet end of said syringe barrel means, such that the pliable material is presented beyond the outlet end of said syringe barrel means in a plurality of individualized sections, each said individualized section being contained in a separate compartment of the divider means, and each said separate compartment having a support surface extending beyond said outlet end of said barrel means to accommodate removal of a selected portion of the sectionalized and compartmentalized part of the material, said divider means comprising a plurality of intersecting planar vanes, each said vane having both a beveled leading edge within said syringe barrel means and a trailing edge beyond the outlet end of said syringe barrel means, said divider means being comprised of a substance having a component that blocks transmission of said activating light; and cap means, comprised of a substance having a component that blocks transmission of said activating light, for selective removal from and placement over said plurality of individualized sections which are presented beyond the outlet end of said barrel means.

35. The syringe apparatus as defined in claim 34, wherein each said individualized section extends substantially less than the distance between said inlet end of the barrel means and the outlet end of the barrel means.

36. The syringe apparatus as defined in claim 34, wherein said divider means is concentric to and has a noncommon longitudinal axis with said barrel means.

37. The syringe apparatus as defined in claim 36, wherein said plurality of intersecting vanes both intersect at and radially extending outward from said noncommon centrally located longitudinal axis.

38. The syringe apparatus as defined in claim 34, wherein said divider means is concentric to and has a common centrally located longitudinal axis with said barrel means.

39. The syringe apparatus as defined in claim 38, wherein said plurality of intersecting vanes both intersect at and radially extending outward from said common centrally located longitudinal axis.

40. The syringe apparatus as defined in claim 39, wherein each said vane has a proximal end and a distal end, the distal end of each said vane serving as a cutting surface for at least one of said individualized sections, each said cutting surface of each said vane extending beyond the outlet end of said barrel means.

41. The syringe apparatus as defined in claims 34 or 40, wherein said barrel means has a cylindrical inside surface extending between the inlet and outlet ends of the barrel means, and wherein each said separate compartment comprises at least a portion of said cylindrical inside surface of said barrel means and at least one of said plurality of intersecting vanes.

42. The syringe apparatus as defined in claim 34, wherein said cap means overlays and essentially seals the outlet end of said barrel means when said cap means is placed over said plurality of individualized sections which are presented beyond the outlet end of said barrel means.

43. The syringe apparatus as defined in claim 42, wherein said barrel means has an external surface and said cap means has an inside surface, said external surface of said barrel means making a sealing contact with the inside surface of said cap means when said cap means is placed over said plurality of individualized sections which are presented beyond the outlet end of said barrel means.

44. The syringe apparatus as defined in defined in claim 43, wherein the inside surface of the cap means defines a space that is large enough so as essentially not to contact said plurality of individualized sections which are presented beyond the outlet end of said barrel means.

* * * * *

UNITED STATES PATENT AND TRADEMARK OFFICE
CERTIFICATE OF CORRECTION

PATENT NO. : 5,387,103
DATED : February 7, 1995
INVENTOR(S) : DAN E. FISCHER

It is certified that error appears in the above-indentified patent and that said Letters Patent is hereby corrected as shown below:

Title page, column 2, item [57], line 16, "discreet" should be --discrete--
Column 4, line 12, "discreet" should be --discrete--
Column 4, line 67, "discreet" should be --discrete--
Column 7, line 20, "discreet" should be --discrete--
Column 11, line 64, claim 23, "as defined in claim 22," should be --as defined in claim 20--
Column 11, line 67, claim 24, "as defined in claim 22," should be --as defined in claim 20--
Column 12, line 12, "radially extending" should be --radially extend--
Column 14, line 3, "radially extending" should be --radially extend--
Column 14, line 11, "radially extending" should be --radially extend--

Signed and Sealed this

Eighteenth Day of July, 1995

Attest:

BRUCE LEHMAN

*Attesting Officer*          *Commissioner of Patents and Trademarks*